United States Patent
Hanks et al.

(10) Patent No.: US 6,182,667 B1
(45) Date of Patent: Feb. 6, 2001

(54) DISPLAY FOR TRANSPORTABLE LIFE SUPPORT SYSTEM

(75) Inventors: Donald Hanks, Woodland Hills; Stephen Francis Jenks, Redondo Beach; Keith Allen Laband, Lakewood; Susan Lynn Marosek, Huntington Beach, all of CA (US)

(73) Assignee: Integrated Medical Systems, Inc., Signal Hill, CA (US)

( * ) Notice: Under 35 U.S.C. 154(b), the term of this patent shall be extended for 0 days.

(21) Appl. No.: 09/285,360

(22) Filed: Apr. 2, 1999

Related U.S. Application Data

(63) Continuation-in-part of application No. 08/667,693, filed on Jun. 21, 1996.

(51) Int. Cl.⁷ .................................................. A61B 19/00
(52) U.S. Cl. .......................................... 128/898; 128/845
(58) Field of Search .................................. 128/845, 696, 128/846, 870, 903; 5/621, 625, 626, 627, 628

(56) References Cited

U.S. PATENT DOCUMENTS

| | | | |
|---|---|---|---|
| 4,161,172 | 7/1979 | Pickering | 128/1 |
| 4,352,991 | 10/1982 | Kaufman | 307/9 |
| 4,680,790 | 7/1987 | Packard et al. | 379/432 |
| 4,715,385 | 12/1987 | Cudahy et al. | 128/710 |
| 4,981,139 | 1/1991 | Pfohl | 128/671 |
| 5,111,818 | 5/1992 | Suzuki et al. | 128/644 |
| 5,307,818 | 5/1994 | Segalowitz | 128/696 |
| 5,331,549 | 7/1994 | Crawford, Jr. | 364/413.02 |
| 5,404,877 | 4/1995 | Nolan et al. | 128/671 |
| 5,421,340 | 6/1995 | Stanga et al. | 128/671 |
| 5,441,047 | 8/1995 | David et al. | 128/670 |
| 5,474,574 | 12/1995 | Payne et al. | 607/7 |
| 5,494,051 | 2/1996 | Schneider, Sr. | 128/870 |
| 5,511,553 | 4/1996 | Segalowitz | 128/696 |
| 5,590,648 | 1/1997 | Mitchell et al. | 128/630 |
| 5,626,151 | 5/1997 | Linden | 128/897 |
| 5,630,238 | 5/1997 | Weismiller et al. | 5/600 |
| 5,664,270 | 9/1997 | Bell et al. | 5/600 |
| 5,687,717 | 11/1997 | Halpern et al. | 128/630 |
| 5,687,734 | * 11/1997 | Dempsey | 128/903 |
| 5,749,374 | * 5/1998 | Schneider | 128/870 |

FOREIGN PATENT DOCUMENTS

PCTAU9500477   2/1996  (AU) .

OTHER PUBLICATIONS

Buchanan Aircraft Corporation Engineered Composites Spectrum Aeromed–Above and Beyond 1995.
Mobi–The Intensive care unit the Results of Innovation–Lifeport, Inc.
Mobile Intensive Care Rescue Facility (MIRF) Aeromed Systems, Inc.—Specification/AMT 300.

* cited by examiner

*Primary Examiner*—Michael A. Brown
(74) *Attorney, Agent, or Firm*—Stetina Brunda Garred & Brucker

(57) ABSTRACT

A method for monitoring information representative of the operation of medical devices such as those of a transportable life support system includes communicating information from a plurality of medical devices to a display via at least one isolation circuit. The isolation circuit(s) mitigate interference with the medical devices so as to facilitate such monitoring without adversely affecting the operation of the medical devices.

7 Claims, 4 Drawing Sheets

DISPLAY FOR TRANSPORTABLE LIFE SUPPORT SYSTEM

RELATED APPLICATION

This patent application is a continuation-in-part patent application of U.S. Ser. No. 08/667,693, filed Jun. 21, 1996, and entitled SELF-CONTAINED TRANSPORTABLE LIFE SUPPORT SYSTEM, the contents of which are hereby incorporated by reference

FIELD OF THE INVENTION

The present invention relates generally to medical devices which are utilized to treat intensive care patients and more particularly to a hand-held display for a self-contained transportable life support system such as those which are utilized in the resuscitation, stabilization, and transport of medical patients. The hand-held display of the present invention interfaces to the medical devices of the transportable life support system in a manner which does not substantially interfere with the operation thereof, thereby attempting to maintain prior governmental approval, such as Food and Drug Administration (FDA) approval of medical devices in the United States.

Thus, according to the present invention, the transportable life support system may not be required to go through the time consuming and expensive governmental approval process, since the individual medical monitoring devices and medical treatment devices thereof have already been approved and since such prior approval may still be valid after integration of the medical monitoring and medical treatment devices into the transportable life support system. Electrical isolation of the medical monitoring devices and medical treatment devices from a common display allows communication of desired parameters from the medical monitoring devices and the medical treatment devices in a manner which does not substantially affect operation thereof and thus potentially maintains prior government approval thereof.

It is important to note that while the intention of this invention is to either maintain prior government approval or at least to substantially simplify any reapproval process, there is no guarantee that such will be the case, since government approval criteria are subject to interpretation and may even change from time to time. Thus, although the present invention attempts to mitigate the need for further government approval, additional approval may be necessary.

BACKGROUND OF THE INVENTION

It is frequently necessary to transport medical patients from the site of an accident or injury to a hospital. For example, persons suffering from various medical emergency conditions such as heart attacks, and strokes must be transported quickly to a medical facility. Medical personnel speak of a "golden hour" within which such a medical patient must be transported to a medical facility so that proper medical care can be provided therefor. The survival rate for such medical patients is greatly enhanced if they are transported to the medical facility within the golden hour.

As those skilled in the art will appreciate, it is frequently difficult to transport a patient to a remotely located medical facility in a timely manner, particularly within the desired golden hour. It is not unusual for accidents to occur at remote locations. Thus, a substantial amount of time may be required to transport the medical patient to a distant hospital. Also, in battlefield situations it is frequently impossible to transport a casualty immediately. In either instance, the patient may be located hundreds, if not thousands, of miles from a hospital, thus necessitating several hours of transport time. As such, it is frequently beneficial to perform various emergency medical procedures at the site of the medical problem, and then to attempt to provide ongoing medical care during transport to a remote hospital. The mortality rate of such transported medical patients is substantially reduced.

It is well-known to use various different medical devices in the field, i.e., at locations remote from a medical facility, so as to enhance a medical patient's chance of survival. For example, it is well-known to use an ECG and a defibrillator upon heart attack victims so as to monitor the condition thereof and so as to provide medical treatment therefor in field.

Typically, the medical patient is placed upon a stretcher and then various different medical devices are used upon the patient, as necessary. During transport the medical devices may either be temporarily disconnected from the patient, or alternatively may be hand carried along therewith by additional personnel. However, disconnection of the medical devices from the patient results in the undesirable disruption of medical monitoring and/or treatment therefor. Hand carrying the medical devices along with the patient requires extra personnel, which may not be available, or for which there may not be adequate room within the transport vehicle.

As such, it is desirable to provide a system for transporting a medical patient wherein the medical devices are carried along with the stretcher. In an attempt to provide such a system for transporting a medical patient while facilitating the continuous use of medical devices thereupon, the Mobile Intensive Care Rescue Facility (MIRF) was developed by the Royal Australian Army Medical Corp. The MIRF is intended to provide sufficient medical equipment to have the capabilities of an intensive care hospital ward. The MIRF is designated so as to facilitate the removal and replacement of the various pieces of medical equipment therefrom for maintenance. The MIRF is specifically designed to accommodate two major roles: the transfer of critically ill people from one point to another, such as from a ward to an x-ray room or from one hospital to another; and the bringing of life support systems quickly to the scene of an accident or other medical emergency.

The MIRF can be configured to include a blood pressure cuff, an invasive blood pressure monitor, a body temperature sensor, a heart rate sensor (finger clip sensor), an oxygen saturation sensor, an exhaled air carbon dioxide sensor, and an electrocardiograph, so as to facilitate medical monitoring of a patient. Further, the MIRF can include a ventilation system, a volumetric infusion pump, a syringe pump, a suction unit, and a defibrillator so as to facilitate medical treatment.

Another contemporary system is the MOBI described in U.S. Letters Pat. No. 4,957,121, issued to Icenogle et al. on Sep. 18, 1990. The MOBI is similar to the MIRF in concept. That is, like the MIRF, the MOBI utilizes off-the-shelf medical devices which are attached to the housing thereof so as to be transportable therewith, thus eliminating disruptions in the medical care provided thereby during transport.

Further examples of such contemporary life support systems include those disclosed in U.S. Pat. Nos. 4,584,989; 4,352,991; 4,691,397; 3,304,116; and 3,341,246.

U.S. Pat. No. 4,584,989 discloses a life support stretcher bed adapted to accommodate patients in intensive or cardiac care units in hospitals. The life support stretcher bed is broadly adapted for electrical medical devices, medical supplies and features an undercarriage including a support structural, wheels, a patient housing with a mattress, an electrical power source and supports for mounting the medical equipment.

U.S. Pat. No. 4,352,991 teaches a life support system adapted for field use in a vehicle with available power and includes electrically operable life support units, means for supporting the life support units, a patient stretcher, and a DC power source adapted for battery or remote power source.

U.S. Pat. No. 4,691,397 teaches a device for carrying the life supporting devices of a bedridden patient including a table like means for supporting the devices, an IV holder, wheeled transport means and a hospital bed footboard securing means.

U.S. Pat. No. 3,341,246 teaches a hospital stretcher adapted broadly with a litter structure having telescopic post elements and other means for manipulating the patient to various positions.

As those skilled in the art will appreciate, it would further be desirable to monitor the operation of each of the medical devices so as to provide both medical personnel with useful information regarding the patient's condition. Medical personnel could then use the results of such monitoring to determine the condition of the patient as well as the treatment which must be provided to the patient.

Thus, when the transportable life system arrives at a medical facility, medical personnel could immediately access a hand-held or fixed display to determine the status of the patient. Rapid access to such information would greatly aid in the diagnosis and treatment of the patient. For example, if the patient has an irregular heart beat then medical personnel would immediately be alerted as to the need to continue with monitoring of the heart beat, as well as to the possible need to treat the irregularity.

The hand-held or fixed display may also be used by maintenance personnel to review an on-board data log so as to determine if the medical monitoring devices were monitoring the patient properly and if the medical treatment devices were applying treatment to the patient in the desired manner. Further, logged parameters such as the time in service for each medical device could be used to provide maintenance personnel with an easy means for determining when routine maintenance should be performed upon each medical device.

However, when the medical devices have previously been approved by a governmental agency such as the Food and Drug Administration (FDA) in the United States, then it is necessary that such monitoring thereof be accomplished without interfering with the operation of the medical devices, so as to attempt to maintain the validity of such prior governmental approval. Merely providing a direct electrical connection between those medical devices for which monitoring is desired and the monitor (or a computer which drives the monitor) is not suitable since such a direct connection has the potential to modify or load-down circuitry of the medical device. As those skilled in the art will appreciate, such modification of the circuitry of a medical device may adversely affect the operation thereof. For example, if the device includes a built in display, then tapping into the signals of that display may weaken the signals, thereby providing a false indication to the display. Thus, any signals associated with the medical devices must be taken in a manner which does not affect the performance of the medical device.

In view of the foregoing, it is desirable to provide a means for monitoring medical devices, i.e., medical monitoring devices and medical treatment devices, of a transportable life support system in a manner which does not invalidate prior governmental approval of the medical devices.

SUMMARY OF THE INVENTION

The present invention specifically addresses and alleviates the above mentioned deficiencies associated with the prior art. More particularly, the present invention comprises a method and apparatus for displaying information representative of the operation of medical devices in a manner which does not substantially affect operation of the medical devices so that prior governmental approval of the medical devices is more likely to be maintained. According to the present invention, at least one isolation circuit facilitates communication from each of a plurality of separate medical devices to at least one hand-held display. The isolation circuits are configured so as to mitigate interference with the medical devices, thereby facilitating monitoring of the medical devices without adversely affecting operation of the medical devices.

According to the preferred embodiment of the present invention, the isolation circuits may comprise either optical isolators or output ports. Those skilled in the art will appreciate that various other isolation devices or circuits are likewise be suitable.

According to the preferred embodiment of the present invention, optical isolators are used to communicate discrete parameters from the medical devices to the hand-held display. As defined herein discrete parameters include signals such as those representing the application of power to the medical device.

As those skilled in the art will appreciate, optical isolators limit the amount of signal which is removed or modified from the light transmitting side of the circuit, i.e., that side of the circuit which is being sensed, and also prevent the introduction of stray or undesirable signals from the light receiving side of the circuit. Thus, the use of such optical isolators substantially limits the effect of such monitoring upon the monitored circuitry.

Similarly, built-in output ports of the medical devices, such as RS-232 ports, are utilized to provide isolation of the medical devices from the monitoring circuitry while communicating logic signals from the medical devices to the hand-held display. As defined herein, logic signals include those signals representative of the functioning of the medical devices, such as signals representative of the monitored condition of the patient as provided by medical monitoring devices and also those signals representative of the therapy provided to the patient by medical treatment devices. It is understood that the distinction between discrete parameters and logic signals is not always clear and that either type of signal may be isolated in either manner, as desired. In some instances, as discussed in further detail below, it may even be desirable to provide both types of isolation, i.e., optical isolation and the use of an output port, so as to better assure complete electrical isolation of a medical device and/or so as to prevent electrical problems which may occur when a common ground is utilized for the medical deice and the transportable life support system.

Thus, according to the methodology of the present invention, medical device monitoring is preformed by providing a first signal representative of a state of a discrete parameter of a medical device to a hand-held display. The step of providing a first signal representative of a state of a discrete parameter of a medical device to a hand-held display comprises the steps of: providing the discrete parameter to an optical isolator so as to cause the optical isolator to define the first signal; and communicating the first signal to the hand-held display.

A second signal representative of at least one logic output of the medical device is also provided. The step of providing the second signal representative of at least one logic output of the medical device comprises the steps of: providing the logic signal to an output port of the medical device so as to cause the output port to define the second signal; and communicating the second signal to the hand-held display. Graphic or text information representative of the first and second signals are then displayed upon the hand-held display.

For example, the step of providing at least one first signal representative of a state of a discrete parameter comprises providing at least one first signal representative of an application of power to a medical device.

According to the preferred embodiment of the present invention, the step of providing the logic signal to an output port comprises providing the output signal to an RS-232 port.

According to the preferred embodiment of the present invention, the hand-held display comprises a personal data assistant (PDA), such as a palmtop computer, for example.

However, it is important to point out that such a palmtop computer is not used to control any of the medical devices. Indeed, the medical devices are not under centralized or common control of any type. Rather, operation of the medical devices is accomplished autonomously.

These, as well as other advantages of the present invention will be more apparent from the following description and drawings. It is understood that changes in the specific structure shown and described may be made within the scope of the claims without departing from the spirit of the invention.

Thus, according to the preferred embodiment of the present invention, a transportable life support system comprises a hand-held display for providing information regarding the condition of the patient, and optionally also provides information regarding the operation of the medical devices thereof.

DETAILED DESCRIPTION OF THE PREFERRED INVENTION

The detailed description set forth below in connection with the appended drawings is intended as a description of the presently preferred embodiment of the invention, and is not intended to represent the only form in which the present invention may be constructed or utilized. The description sets forth the functions and the sequence of steps for constructing and operating the invention in connection with the illustrated embodiment. It is to be understood, however, that the same or equivalent functions may be accomplished by different embodiments that are also intended to be encompassed within the spirit and scope of the invention.

The hand-held display for a transportable life support system of the present invention is illustrated in FIGS. 1 through 4 which depict a presently preferred embodiment thereof.

Figure 1:
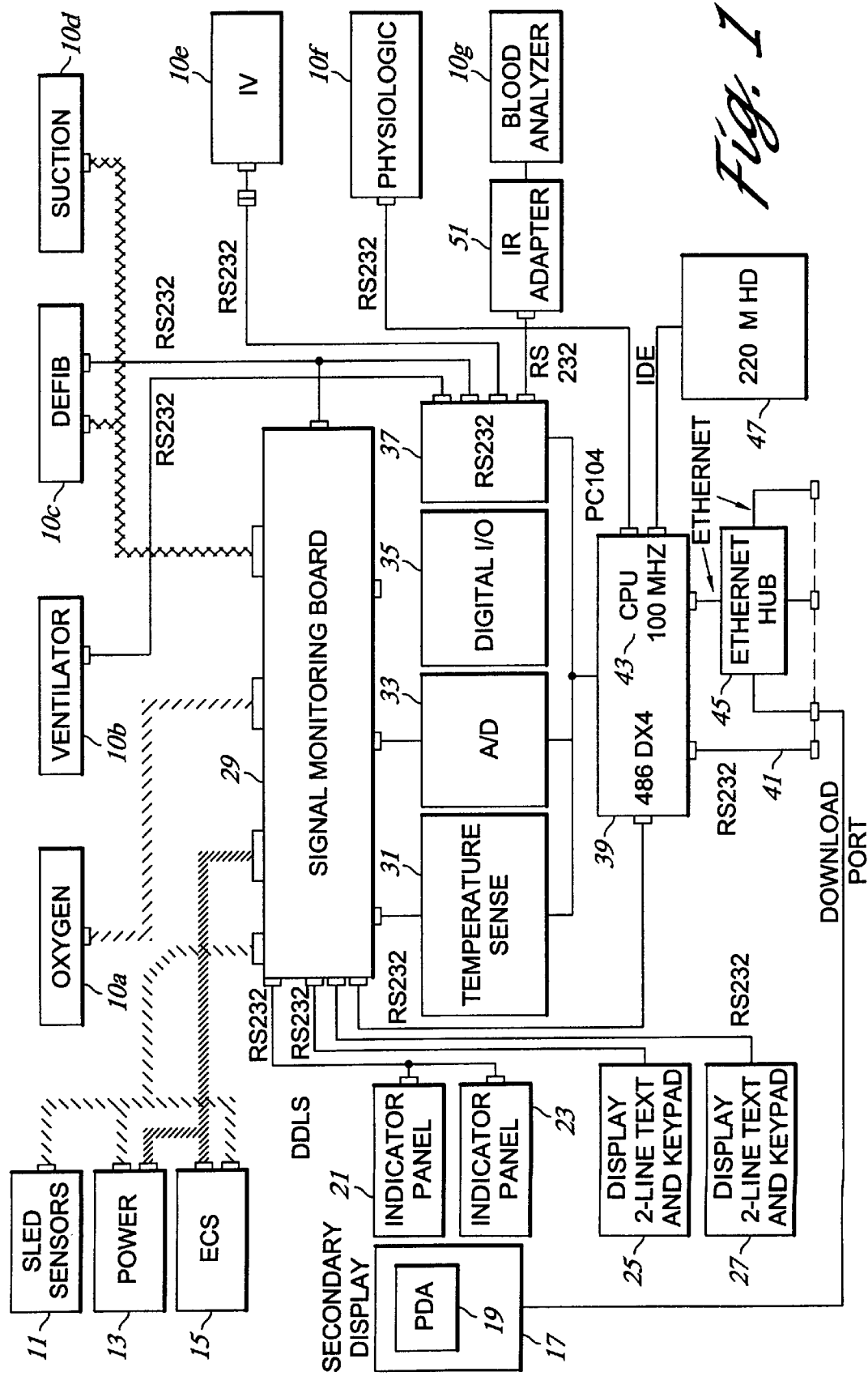
FIG. 1 is a block diagram showing the interconnection of exemplary medical devices, i.e., medical monitoring devices and medical treatment devices, with a hand-held display in a manner which does not adversely affect the operation of the medical devices.

Referring now to FIG. 1, a plurality of medical devices 10*a*–10*g*, including both medical monitoring devices and medical treatment devices, are in electrical communication with the hand-held display or personal data assistant (PDA) 19 such that the operation of the medical devices 10*a*–10*g* may be monitored. As discussed in detail above, such monitoring of the operational parameters associated with the medical devices 10*a*–10*g* facilitates both enhanced patient care and enhanced maintenance of the medical devices 10*a*–10*g*.

According to the preferred embodiment of the present invention, discrete parameters associated with the medical devices 10*a*–10*g* are monitored via optical isolators (105 of FIG. 2, for example) and logical outputs of the medical devices 10*a*–10*g* are monitored via built-in RS-232 ports of the medical device's 10*b*–10*g* themselves. In this manner, critical parameters associated with the medical devices 10*a*–10*g* are monitored and also optionally logged without interfering with the proper operation of the medical devices 10*a*–10*g* and also potentially without invalidating prior governmental approval of the medical devices 10*a*–10*g*. Each medical device 10*a*–10*g* may utilize either an optical isolator or a built-in RS-232 port, or a combination of both, as desired. According to the preferred embodiment of the present invention, medical devices 10*a*–10*g*, such as oxygen 10*a*, and ventilator 10*b*, provide their discrete parameters to the storage device 47 and to the PDA 19 via signal monitoring board 29, which provides an electrical interface therefore. No means is provided for the PDA 19 to control any of the medical devices. The signal monitoring board 29 provides signal conditioning for the discrete parameters and also may facilitate additional functionality, such as the triggering of audible alarms when such discrete parameters indicate an undesirable condition of the medical devices 10*a*–10*g*.

According to the preferred embodiment of the present invention, a 100 MHz 486 PC single board system is utilized to control the system. The board 39 preferably incorporates several expansion board equivalents, including video processing, IEEE 802.3 Ethernet and SCSI Interfaces, IDE Controller, and serial port interfaces, which are included on a single board, low powered, 8.0×5.75 inch footprint. The board 39 preferably uses the PC-104 expansion bus standard to add hardware modules for functional expansion.

Four PC-104 interface modules are incorporated into the design to allow the data logger and PDA 19 to communicate with the medical devices. According to the preferred embodiment of the present invention, a custom-printed signal monitoring board is utilized to provide signal conditioning and interfacing between the AMPRO board 39 and the medical devices 10*a*–10*g*, according to well known principles.

According to the preferred embodiment of the present invention, the interface capability of the signal monitoring board 29 facilitates the acquisition of information from up to 8 RS-232 serial ports, 64 digital ports, 35 analog ports, and 8 temperature ports. Data from all of these interfaces may be acquired and processed by the AMPRO CPU 43 and then stored on one 220 MByte ruggedized hard drive 47. As those skilled in the art will appreciate, various other means for storing the acquired data may be utilized.

Further, according preferred embodiment of the present invention the data logging system comprises an Ethernet interface to facilitate remote connections, efficient downloading of the log data, and reel time display of selected information to secondary display units 17, such as a PDA 19.

The Ethernet interface 45 allows a logistics operator to perform maintenance activities on the embedded device or to network a number of such transportable life support systems within a single nurses station.

According to the preferred embodiment of the present invention, the data logging system is activated any time that power is turned on for the transportable life support system. Thus, no special action is required of an operator in order to initiate continuous data logging. Additionally, the hand-held display may be utilized any time that power is turned on, whether or not a patient is disposed upon the transportable life support system. Thus, the PDA 19 may be utilized to verify proper functioning of the medical instruments, check the calibration thereof, etc. Indeed, according to the preferred embodiment of the present invention, the PDA 19 may be operated in a training mode wherein the presence of a patient is simulated so as to facilitate training of personnel. Thus, for example, various different problems may be simulated via the PDA 19. The PDA 19 then checked for the proper response from attending personnel.

Oxygen sensor 10*a* facilitates monitoring of the level of oxygen saturation of the patient's blood. Ventilator 10*b* assists the patient in breathing. Defibrillator 10*c* provides defibrillation to the patient's heart, as needed. Suction 10*d* is utilized to remove undesirable fluid from the patient (from the patient's lungs or a wound, for example). IV 10*e* provides for the infusion of fluids into the patient. Physiological monitoring 10*f* facilitates the monitoring of various physiological parameters according to well known principle's. Blood analyzer 10*g* analyzes desired parameters of the patients blood.

Sled sensors 11 monitor various aspects of the transportable life support system, such as the temperature of critical components thereof. Power 13 provides power to the electrical components of the transportable life support system. The Environmental Control System (ECS) 15 provides heating and/or cooling to the various devices of the transportable life support system, as required.

As mentioned above, the secondary display 17 preferably comprises a personal data assistant (PDA) 19 which is optionally used to monitor the status of the patient and transportable life support system. However, those skilled in the art will appreciated the various different types of display devices are likewise suitable. For example, a liquid crystal display, a small CRT, a portable or lap-top computer, etc. may be utilized. However, in no instance does such a portable or lap-top or any other computer control operation of the medical devices.

A Data Display and Logging System (DDLS) comprises an indicator panels 21 and 23 which provides indications representative of the operation of the medical monitoring and medical treatment devices. Display 2-line text and keypads 25 and 27 facilitate data entry for control of the medical monitoring and treatment devices.

According to the preferred embodiment of the present invention, signal monitoring board 29 provides an interface for the medical monitoring and treatment devices and the controls and displays therefore, according to well known principles. Temperature sensing system 31 facilitates the sensing of temperatures at various locations of the transportable life support system. A/D converter 33 facilitates interface of the signal monitoring board 29 with CPUs 41 and 43. It is important to note that CPU's 39 and 43 do not function to I. Control any medical treatment devices. Indeed, none of the medical treatment devices of the present invention are controlled by a CPU which is not a part of the device itself. That is, the medical treatment devices of the present invention are not under common control.

Similarly, digital IO 35 facilitates interface of the signal monitoring board 29 with CPUs 41 and 43. RS-232 interface facilitates interface of the ventilator 10*b*, the defibrillator 10*c*, IV 10*e*, and blood analyzer 10*g*, with the CPU 39. CPU 39 preferably comprises a 486 DX4 41 driven by a 100 MHZ CPU clock 43.

According to the preferred embodiment of the present invention, an RS-232 port 44 and an Ethernet hub 45 facilitate communication between the transportable life support system and other devices, such as computers, communications equipment, and other transportable life support systems. The secondary display 17 is preferably interfaced with the transportable life support system via Ethernet hub 45. However, those skilled in the art will appreciate that the secondary display 17 may be interfaced with the transportable life support system via various different means.

The storage devices of the present invention preferably comprise one 220 MByte hard drive 47 which is in electrical communication with the CPU 39.

According to the preferred embodiment of the present invention, the blood analyzer 10*g* communicates via infra red (IR) adaptor 51. The IR adaptor 51 comprises an RS-232 port to facilitate communications with the RS-232 interface 37.

Figure 2:
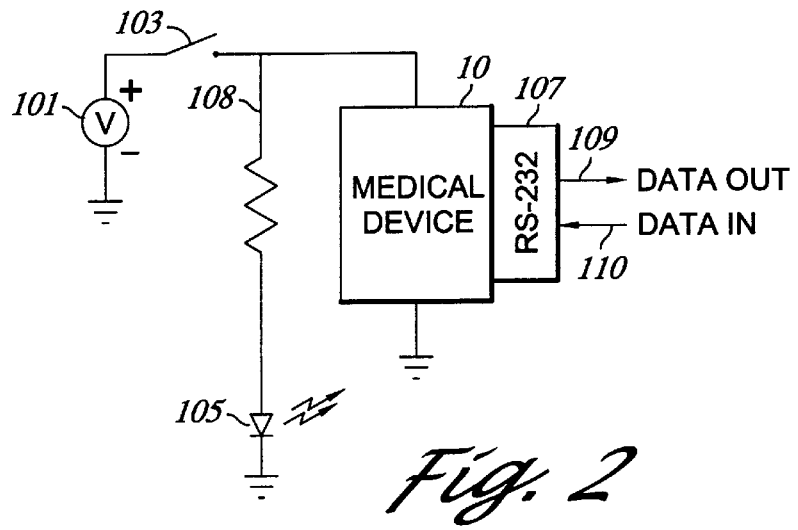
FIG. 2 is an electrical schematic showing the interface of an exemplary medical device to a hand-held display.

Referring now to FIG. 2, the present invention generally comprises a hand-held display or PDA 19 (FIG. 1) for receiving information from a medical device 10 in a manner which does not impart autonomous control functionality of the medical device 10. Note that the medical device 10 is a generic reference to any of the medical devices 10*a*–10*g* of FIG. 1. Thus, any of the medical devices 10*a*–10*g* may be interconnected to the PDA 19 via either an optical isolator 105 or a built in RS-232 port 107 (or a similar built in output port) as desired an/or as dictated by the medical device (as determined by whether or not the medical device is provided with a built-in RS-232 output port). The data out 109 and data in 110 lines for RS-232 port 107 thus facilitate bi-directional communication with the PDA 19 of FIG. 1. As shown in FIG. 1, such communication is preferably via ethernet hub 45, CPU 39, A/D 33, digital IO/35, RS-232 37, and/or signal monitoring board 29.

The present invention comprises an interface to the medical device 10 which facilitates monitoring of the medical device 10 in a manner which does not adversely affect the operation thereof. According to the preferred embodiment of the present invention, the interface comprises an optical isolator 105 which provides a signal representative of the status of the application of a discrete or power signal to the medical device 10. Thus, when power is applied from power source 101 via switch 103 to medical device 10, then optical isolator 105 provides a signal to the hand-held display as PDA 19 of FIG. 1. Resistor 107 defines the working voltage of optical isolator 105.

Optionally, the medical device 10 further comprises an RS-232 port 107 which provides at least one output 109 and optionally one or more inputs 110. Each output 109 of RS-232 port 107 provides a data channel for logical signals, such as those representative of medical treatment provided by medical treatment devices and measure parameters measured by medical monitoring devices.

Figure 3:
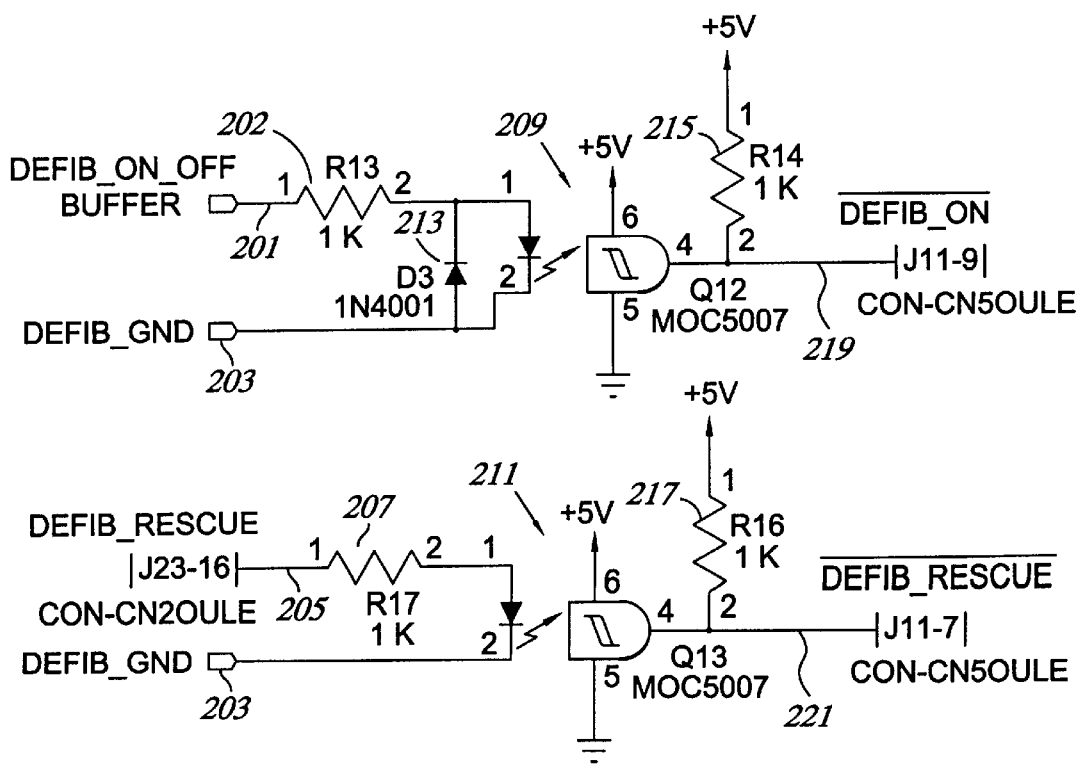
FIG. 3 is a schematic showing the interconnection of a medical device to a hand-held display in further detail.

Referring now to FIG. 3, an example of the use of optical isolators 209, 211 for a particular medical device, i.e., the defibrillator, is shown. In this example two discrete parameters are monitored. DEFIB_ON_OFF_BUFFER is a signal which indicates whether or not the defibrillator has power applied thereto. According to the preferred embodiment of the present invention, the application power to the defibrillator results in the application of power to optical isolator 209. Current limiting resistor 202 regulates the amount of current which flows through optical isolator 209 and protection diode 213 provides over-current protection therefor. The output of optical isolator 209 is representative of the status of the application of power to the defibrillator. Thus, when power is not applied to the defibrillator, then no current flows through optical isolator 209 and no output signal is provided therefrom, thus allowing the output thereof to be pulled positive through resistor 215. The application of power to the defibrillator causes the output of the optical isolator 209 to be pulled to ground. Those skilled in the art will appreciate that various other configurations of the optical isolator 209 are likewise suitable.

The second discrete parameter associated with the defibrillator is the DEFIB-RESCUE signal which is representative of the application of defibrillation current to the patient. The DEFIB-RESCUE circuit is similar to the DEFIB-ON-OFF-BUFFER circuit with the exception that an over compensation diode is not required since the power level is lower. Thus, the application of a DEFIB-RESCUE signal to the input 205 of the circuit causes current to pass through resistor 207 to ground 203, thereby actuating optical isolator 211. As in the DEFIB-ON-OFF-BUFFER described above, plus 5 volts sensed at output 221 via resistor 217 until the optical isolator 211 is actuated. The optical isolator 211 then pulls output 221 to ground, thereby indicating the application of defibrillation current to the patient.

Figure 4:
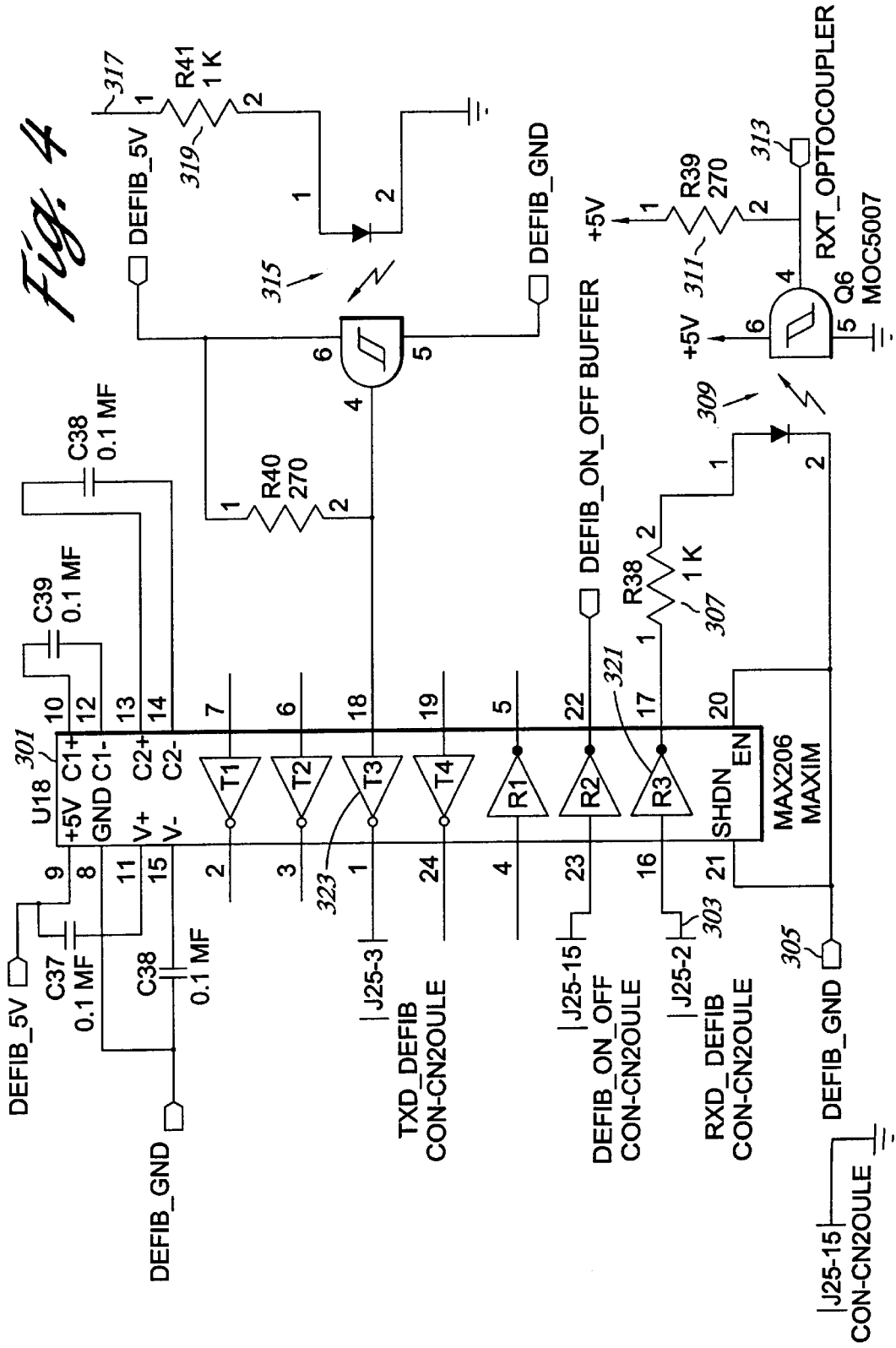
FIG. 4 is a schematic showing the interconnection of a medical device to a hand-held display in further detail.

Referring now to FIG. 4, and RS-232 output port 301 for providing logic signals from a medical device to the storage device 47 and/or the PDA 19 is shown. The RS-232 port comprises inverters 323, 321 which provide buffering and isolation for signals transmitted to and from the RS-232 port so as to mitigate undesirable interference with the medical device.

The RXD-DEFIB signal, which indicates that defibrillation is being performed, is thus isolated from the PDA 19 via invertor 321 of the RS 232 port 301.

According to the preferred embodiment of the present invention, the defibrillator is completely electrically isolated from the PDA 19, thus necessitating the further use of optical isolators 309 and 315. This is due to the extremely high voltage as generated by the defibrillator. Other medical devices do not generally require such additional isolation. It will further be appreciated that the display may be fixed to the transportable life support system rather than be hand held. Thus, according to the preferred embodiment of the present invention, the RDX-DEFIB signal is isolated or buffered by both the RS-232 output port 301 and optical isolator 309. The output 313 of the optical isolator 309 is thus electrically isolated from the defibrillator. A logical input 317 TXT-DEFIB to the defibrillator is provided through resistor 319 to optical isolator 315 and invertor 323 of RS 232 port 301 in a similar fashion. In this manner, both logical inputs and outputs to the defibrillator 10c are completely electrically isolated from the remainder of the transportable life support system.

Thus, according to the present invention, both discrete parameters and logic signals associated with medical devices 10 are monitored and stored in a manner which does not adversely affect operation of the medical device 10 and thus potentially does not invalidate prior governmental approval thereof.

Figure 5:
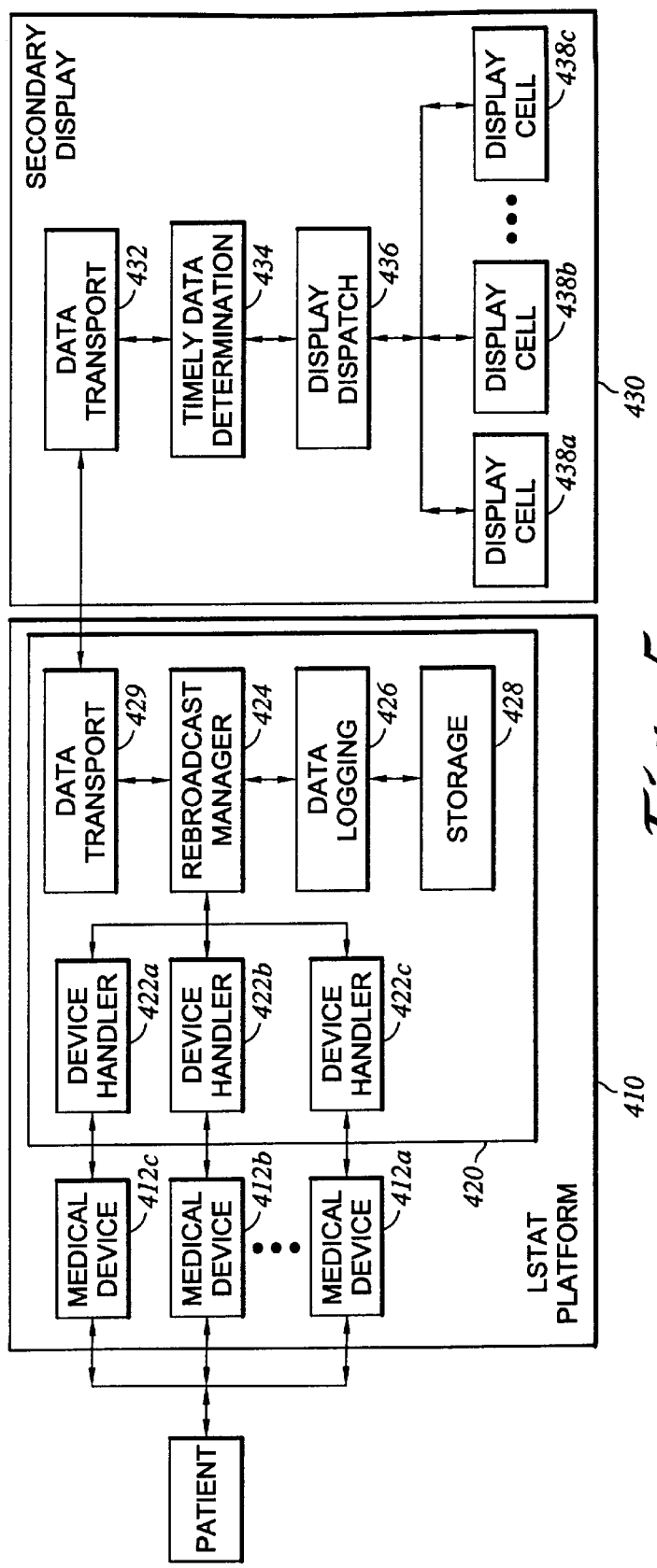
FIG. 5 is a functional block diagram illustrating the operation of the invention.

FIG. 5 is a functional diagram illustrating a display device in accordance with the present invention, and supporting devices. FIG. 5 illustrates the end-to-end transactions that take place to generate features of the present invention. FIG. 5 illustrates a medical platform 410 with an embedded data display and logging system (DDLS) 420. The DDLS 420 accepts data from the medical devices 412a, 412b, 412c, via device handlers 422a, 422b, 422c. The device handlers manage low-level protocols with the medical devices on a non-interference basis and checked for transmission errors. The data is wrapped with further error-checking information relayed to a rebroadcast manager 424. The rebroadcast manager does a one-to-many mapping of any subset of data. The data is then delivered to data logging device 426 in storage unit 428. The data is also delivered from rebroadcast manager 424 to data transport device 429, which communicates data to the secondary display 430. The secondary display receives the data via data transport device 432 and applies various checks, at timely data determination device 434, to insure proper transmission and timeliness of data. Erroneous data is discarded and an error indication is substituted for bad data. A bad data indication is generated by display dispatch device 436 and illustrated at one or more display cells 438a, 438b, 438c. A display cell may be viewed as an individual element of an overall display screen, e.g., a temperature graph within an overall patient summary screen. Correct data (or an error indication) may be decoded and dispatched to the destination display cell. Each display cell interprets its received data and generates the proper display. Multiple parallel display cells may be utilized to create a display montage derived from multiple medical devices' data. This montage may be reconfigurable, or fixed into a static display.

Accordingly, a display system in accordance with the present invention may provide summary data as well as detailed data from a variety of medical devices. It montages information from multiple devices to create a display that cannot be derived from data generated from a single medical device. Information (e.g., system health and safety data, electrocardiograms side-by-side with ventilation information) can be displayed together and/or integrated into new information. Such a system can be applied to operating rooms, trauma centers, emergency rooms and elsewhere. Moreover, the system may be implemented in tele-medical applications as well.

The function of a display system in accordance with the present invention may therefore be summarized as follows:

1. Data generated by medical device, and accepted by data handler.
2. Data check for transmission errors.
3. Data wrapped with packing information.
4. Data subsets transmitted and individually addressed to each display cell based on subscription by display cell. Multiple display cells can subscribe to the same piece of data (one-to-many data distribution).
5. Data destined for remote users are delivered via the data transport mechanism.

6. Data received by display processor.

7. Data unpacked, checked for transmission errors, and checked for timeliness.

8. If data has errors, then error indication is dispatched to display cell and the original data is discarded.

9. If data is validated, then data is decoded and passed to display dispatch.

10. Data arranged and applied to display cells, error indications are displayed as appropriate (e.g., gray bars for graphs, or de-emphasized fonts for text).

Accordingly, the present invention provides apparatus and technique for assimilating data from a plurality of independent medical devices, by tapping signal streams within the devices that may not normally be available for medical device output. Those signals are then communicated to a common display device, where they can be illustrated individually, in combination, or interrelation. Processing the data from the medical devices may be effected intermediate the medical device and the display. Data communicated to the display may be formatted to the display as desired. Moreover, the display may be implemented in a manner to facilitate generation of commands at the display, to direct the processor to display, arrange, or interrelate data as desired.

Referring now to FIG. 5, a functional diagram illustrating the process overview of the invention, is shown therein. The process of the present invention begins with the medical devices and ends with logged in display data. The existing medical devices 401a, 401b, 401c that operatively monitor patient 400, gathering and processing medical data normally. Instrumentation and data monitors interface with the medical devices to extract that data nonintrusively, by using software and hardware techniques. This minimal impact to the medical devices is important because it allows the invention to leverage existing Food and Drug Administration (FDA) pedigree of the medical devices. The medical devices 401a, 401b, 401c communicate information to the device handlers 403a, 403b, 403c. The device handlers, using a common time base, timestamp the data from the time the medical devices deliver the data to the rebroadcast manager 405, a central distribution point. The common timestamps provide the basis for synchronization of the data for later clinical analysis. This is important because new treatment algorithms can be created from this data into the common time base line.

The rebroadcast manager 405 then relays the data to the data transport device 407, archive manager 413, and data logging device 409. The central distribution point of rebroadcast manager 405 is further important because it insures that the data being displayed and the data being logged are identical. The data transport device 407 communicates the data to secondary display 411. The secondary display then collects the received data into a coherent format. The data archive manager 413 provides a caching of data for quick retrieval by the secondary display. The archive manager 413 implements a virtual medical device that records important data—for instance, to implement a trending display of medical parameters. Consequently, data can be broken down and recombined in various and differing ways. The data logger 409 records data in secondary storage device 415 for later retrieval. The secondary storage device 415 can be accessed via FTP client 417 and FTP server 419.

It is understood that the exemplary display for a transportable life support system described herein and shown in the drawings represents only a presently preferred embodiment of the invention. Indeed, various modifications and additions may be made to such embodiment without departing from the spirit and scope of the invention, for example, those skilled in the art will appreciate that various isolation means are equivalent to the use of an optical isolator. For example, an acoustic isolator or a mechanical isolator may similarly be utilized. Further, various types of output ports may be utilized in place of an RS-232 port and thus are considered equivalent to an RS-232 port and may be used instead. Thus, these and other modifications and additions may be obvious to those skilled in the art may be implemented to adapt the present invention for use in a variety of different applications.

What is claimed is:

1. A method for monitoring information representative of operation of medical devices, the method comprising the steps of:
   a) providing a first signal representative of a state of a discrete parameter of a medical device to a display, the step of providing a first signal representative of a state of a discrete parameter of a medical device to a display comprising the steps of:
      i) providing the discrete parameter to an optical isolator so as to cause the optical isolator to define the first signal;
      ii) communicating the first signal to the display;
   b) providing a second signal representative of at least one logic output of the medical device, the step of providing a second signal representative of at least one logic output of the medical device comprising the steps of:
      i) providing the logic signal to an output port of the medical device so as to cause the output port to define the second signal;
      ii) communicating the second signal to the display; and
   c) displaying information representative of the first and second signals upon the display;
   d) wherein the steps of providing the discrete parameter to an optical isolator and providing the logic signal to an output port facilitate monitoring of the medical devices in a manner which mitigates interference with operation of the medica devices so as to maintain a reliability and effectiveness thereof.

2. The method as recited in claim 1, wherein the step of communicating information from a plurality of medical devices to the display via at least one isolation circuit comprises communicating information from a plurality of medical devices to the display via at least one of an optical isolator and an output port.

3. The method as recited in claim 1, wherein the step of communicating information from a plurality of medical devices comprises communicating information from a plurality of medical devices disposed upon a transportable life support system.

4. The method as recited in claim 1, wherein the step of communicating information from the plurality of medical devices to the display comprises communicating information to a PDA.

5. The method as recited in claim 1 wherein the step of providing at least one first signal representative of a state of a discrete parameter comprises providing at least one first signal representative of an application of power to a medical device.

6. The method as recited in claim 1, wherein the step of providing the logic signal to an output port comprises providing the output signal to an RS-232 port.

7. The method as recited in claim 1, wherein the step of providing a second signal further comprises the steps of providing an output of the output port to an optical isolator so as to define the second signal.

* * * * *